United States Patent [19]

Muller et al.

[11] Patent Number: 5,037,378

[45] Date of Patent: Aug. 6, 1991

[54] PROCESS FOR COATING A FLEXIBLE TUBULAR PROSTHESIS WITH LIVING CELLS

[75] Inventors: Werner Muller, Wiesendangen; Marie-Claude Hensel, Bertschikon; August Huber, Raterschen, all of Switzerland

[73] Assignee: Sulzer Brothers Limited, Winterthur, Switzerland

[21] Appl. No.: 412,083

[22] Filed: Sep. 25, 1989

[30] Foreign Application Priority Data

Oct. 7, 1988 [CH] Switzerland .................. 3751/88

[51] Int. Cl.$^5$ ............................................. A61F 2/04
[52] U.S. Cl. ........................................... 600/36; 623/1; 623/15; 435/240.23; 435/240.242; 435/177; 435/180
[58] Field of Search ............. 435/240.21, 240.23, 435/240.242, 240.243, 177, 180; 623/1, 15; 600/36

[56] References Cited

U.S. PATENT DOCUMENTS 4,418,691 12/1983 Yann et al. .................. 623/15 X
4,546,500 10/1985 Bell ................................. 623/1

FOREIGN PATENT DOCUMENTS 1074579 4/1986 Japan ..................... 435/240.23
82/03764 11/1982 PCT Int'l Appl. .
8803560 5/1988 World Int. Prop. O. .

Primary Examiner—Randall L. Green
Assistant Examiner—Paul Prebilic
Attorney, Agent, or Firm—Kenyon & Kenyon

[57] ABSTRACT

The coating process for coating the vascular prosthesis resides in stepwise rotations of the prosthesis, filled with a cell suspension, through fixed angles and in pauses for deposition between the rotations. The length of pauses start at two seconds and are increased in small increments of from 1 to 2 seconds to values of 2 to 3 minutes. The angle of rotation is controlled to ensure a uniform gapless deposition of the living cells.

11 Claims, No Drawings

PROCESS FOR COATING A FLEXIBLE TUBULAR PROSTHESIS WITH LIVING CELLS

This invention relates to a process for coating a flexible tubular prosthesis. More particularly, this invention relates to a process for coating a flexible tubular vascular plastic prosthesis with living cells.

Heretofore, various techniques have been known for the coating of vascular prostheses with living cells, for example, as described in German OS 3637260 and WO82/03764. However, the techniques described have been rather complicated and cumbersome.

Other techniques have also been known wherein living cells are seeded as an aqueous suspension in a physiological solution in a vascular prosthesis and deposited in the prosthesis by gravity. In such cases, the prosthesis is usually previously coated with an extra cellular matrix, and disposed in a horizontally stretched position. In addition, the suspension filled prosthesis is rotated about a longitudinal axis in steps which are interrupted by pauses for deposition of the cells.

This process is conventional for coating flexible tubular prostheses with living cells, particularly with single layers of epithelial cells. However, it has been found in practice that even with a wide range of variations of the angles of stepwise rotation and/or of the duration of the pauses for deposition, cells are not deposited uniformly on the prosthesis inner wall. Instead, striations occur and the coatings fail to provide reproducible results.

Accordingly, it is an object of the invention to ensure that the cells are always deposited uniformly in the peripheral direction and that the prosthesis inner wall is always coated gaplessly (confluently).

It is another object of the invention to be able to apply a uniform coating of living cells to the interior of a vascular prosthesis.

It is another object of the invention to achieve a high efficiency of removal of all cells which are living and capable of living from a suspension for coating a vascular prosthesis.

Briefly, the invention provides a process for coating a flexible tubular vascular plastic prosthesis with living cells. In accordance with the process, the interior of a tubular process is seeded with a cooled cell suspension at a temperature sufficient to preclude precipitation of cells from the suspension, for example at a temperature of below 5° C.

Thereafter, the suspension-filled prosthesis is heated to approximately body temperature while being rotated about a horizontally disposed longitudinal axis in order to homogenize the suspension and prevent premature uncontrolled deposition of the cells.

Next, the rotation of the prosthesis is interrupted from a short deposition pause of at most two seconds in order to permit sedimentation of cells onto the interior surface of the prosthesis. Thereafter, the prosthesis is sequentially rotated over a predetermined angle and rotation is interrupted for predetermined pauses of time over a predetermined time in order to permit deposition of the cells from the suspension in prosthesis without the occurrence of a peripheral striation.

Thereafter, the prosthesis is continuously rotated while the suspension is extracted with the remaining unprecipitated cells therein.

The prosthesis may be made of any suitable material such as one of the plastics normally used in the vascular prosthesis art.

The low temperature at the commencement of seeding, that is, when the prosthesis is filled with a cell-containing aqueous suspension in a physiological solution, ensures that the prosthesis is not covered with cells during the preparation phase for the actual coating steps.

After the temperature has reached approximately body temperature, for example, 37° C., starting from a first short pause for deposition in which there is definitely still no deposition of cells, the pauses between the discrete rotations are consecutively increased stepwise, the pause not necessarily having to be increased at each step. The pause increases are always small—between 1 and 2 seconds—and can be constant but are not necessarily constant. As a result of these stepwise increases in pause length, all the cells whose deposition times or rates within a row of cells and in various cell rows form a complete spectrum, which may also depend upon the stage of cell growth, have the opportunity of being deposited.

The predetermined angle over which the prosthesis is rotated may be an angle other than $\pi$. In this respect, the predetermined angle should be an unremaindered fraction of $\pi$ without a common divisor. For example, the angle maybe in the range of from $4/5\pi$ to $8/9\pi$ or in the range of from $10/9\pi$ to $6/5\pi$.

The criteria for the angles of the between-pauses rotations ensure that each wall element experiences, on the average, an equal duration of deposition action in the peripheral direction, the specified limits ensuring that peripheral striation cannot occur either as a result of overlapping or as a result of voids between angle zones which experience a deposition of cells in the discrete pauses. The angles of rotation can be increased by integral multiples of $2\pi$ without impairment of the effect of the process; such increases may even be advantageous since they lead to thorough mixing of the cells and therefore to intermediate homogenization of the suspension.

Another effect of angles of rotation close to $\pi$ is that cells of every rate of deposition i.e., cells which are deposited fast and cells which are deposited slowly, are deposited consecutively in distributed form over the entire periphery in all zones. In this connection, angles of rotation of $4/5\pi$ or $6/5\pi$ associated with deposition zone $\pi/5$ on the periphery during a pause have proved very advantageous.

When the pauses have finally reached values of several minutes, for example, between 2 and 3 minutes, the suspension contains only very slowly precipitating, damaged and dead cells which must be removed. Deposition of the cells still present in the suspension is obviated by the continuous further rotation of the prosthesis until extraction of this residual suspension.

The process can be used with advantage to coat a prosthesis with a single layer of epithelial cells, for example endothelial cells, or with one or more layers of one or more types of cell.

Conveniently, depending on the plastics used for the prosthesis, for example, porous polyurethane, the prosthesis is given an equilibration treatment before any coating in which the outer surface and inner surface of the plastics tube, and the plastics itself, are brought into equilibrium with the ambient liquid are water-saturated, for example, to open the pores and make them permeable.

These and other objects and advantages of the invention will become more apparent from the following detailed description.

Initially, it is assumed that a vascular prosthesis embodied by a flexible plastic tube produced in a manner as described in U.S. patent application Ser. No. 278806 is to be coated with a single layer of endothelial cells. Further, the coating process is to be performed in a treatment chamber such as that described in U.S. patent application Ser. No. 278807, in which the prosthesis is stretched out lengthwise and is rotatable around a longitudinal axis, the same not necessarily being concentric of the prosthesis axis. The drive for rotating the prosthesis is in known manner, for example, a conventional stepping motor having a shaft connected to the treatment chamber.

Initially, the prosthesis is given an equilibration treatment in order to saturate the prosthesis wall with water and to open all the pores. For this preliminary treatment, the completely uncoated prosthesis is first autoclaved in bidistilled water, whereafter the outer space and inner space in the treatment chamber near the prosthesis are filled with HBS-2, a known buffer solution. HBS-2 is a physiologically buffered saline solution called "Hepes buffered saline" but is also modified with calcium chloride and magnesium chloride. This treatment is given at ambient temperature without special thermostatic provision and resides merely in that the solution-filled plastics prosthesis is left to stand for a few days, for example, three days, the time depending upon the nature of the plastics and the prosthesis wall structure.

The equilibrated prosthesis is then treated in known manner by pre-coating the interior with an extra-cellular matrix consisting in known manner of fibronectin, collagen, laminin, elastin or thrombospondin or natural or defined mixtures of individual ones of these and other substances. In the present example, fibronectin is used for the pre-coating. Coating is performed by a method conventional for the coating of culture vessels. First, the buffer solution of the equilibration treatment is removed from the treatment chamber and prosthesis and the same is filled with a fibronectin solution. Thereafter, the buffer solution is introduced into the outer space of the chamber around the prosthesis to ensure that the prosthesis wall does not dry out from the outside.

After the fibronectin solution has acted for a conventional period of, for example, approximately 45 minutes on the prosthesis inner wall at ambient temperature, the filled treatment chamber is stored in a refrigerator or placed in ice water until its temperature has been reduced to approximately 4° C.

The next step is the seeding of the endothelial cells in the fibronectin-coated prosthesis. The buffer solution and fibronectin solution are removed from the cooled treatment chamber and the prosthesis interior space is filled with a cell suspension that has also been cooled to 4° C. The cells show no tendency to precipitate in the suspension at this low temperature. The cell consumption is in known manner approximately $10^5$ cells/cm$^2$ of prosthesis surface to be coated. A conventional nutrient solution is introduced into the outer space of the prosthesis, such solution being, for example, a commercially available physiological nutrient and culture solution.

The prosthesis treated as described and the still cooled treatment chamber are then connected to the stepping or positioning motor (not shown) and the prosthesis inner wall is then coated with the cells. The first partial step in this connection is to heat the complete treatment chamber to approximately body temperature—i.e. approximately 37° C.—while the chamber rotates continuously at from 20 to 50 rpm, more particularly, e.g. 33 rpm; the continuous rotation obviates sedimentations with the cell suspension.

Once the required body temperature has been reached, sedimentation of the cells begins with a two-second pause followed by a rotation through $6/5\pi$. The rotation is followed by another pause for sedimentation which is about 1 to 2 seconds longer before there is a further rotation through $6/5\pi$. Alternating with pause increases in increments of 1 to 2 second—the increments can be made at each step or only after 2 or 3 steps—the prosthesis continues to be rotated through the same angle until the pause times have reached approximately 2 to 3 minutes. The total coating time is therefore several hours during which the entire prosthesis is given a uniform internal coating of endothelial cells which, after having been spread out, cover the prosthesis uniformly and gaplessly. Fast settling and slow settling cells are distributed substantially uniformly over the entire periphery so that there is a uniform coating on the entire surface.

Upon completion of coating, the suspension contains only very slow settling, non-viable and dead residual cells which must be extracted. After coating, therefore, the treatment chamber continues to rotate continuously at a speed of from 1 to 5 rpm to ensure that these residual cells are not precipitated on the coated prosthesis.

During this after treatment or immediately after the rotating mechanism has stopped, the cell-depleted suspension containing the residual cells is extracted.

The coated prosthesis is then given a conditioning treatment in the same treatment chamber, as described, for example, in U.S. patent application Ser. No. 278807.

The invention thus provides a relatively simple process for applying a uniform coating of living cells on the interior surfaces of a tubular vascular prosthesis.

Further, the invention provides a process for uniform covering of the inner wall of a prosthesis with an unstriated and gapless layer of living cells.

What is claimed is:

1. A process for coating a flexible tubular vascular plastic prosthesis with living cells, said process comprising the steps of
    seeding the interior of the tubular prosthesis with a cooled cell suspension at a temperature sufficient to preclude precipitation of cells from the suspension;
    heating the suspension-filled prosthesis to approximately body temperature while rotating the prosthesis about a horizontally disposed longitudinal axis thereof to prevent premature uncontrolled deposition of cells;
    interrupting rotation of the prosthesis for a short initial pause of at most two seconds to permit sedimentation of cells onto the interior surface of the prosthesis;
    thereafter sequentially rotating the prosthesis over a predetermined angle and interrupting rotation of the prosthesis for predetermined pauses of time over a predetermined time to permit deposition of cells from the suspension in at least one uniform layer on the interior surface of the prosthesis without the occurrence of a peripheral striation; and
    thereafter continuously rotating the prosthesis while extracting the suspension with the remaining unprecipitated cells therein.

2. A process as set forth in claim 1 wherein said predetermined angle is other than $\pi$.

3. A process as set forth in claim 1 wherein said predetermined angle is an unremaindered fraction of $\pi$ without a common divisor.

4. A process as set forth in claim 1 wherein said predetermined time is of several hours duration.

5. A process as set forth in claim 1 wherein said predetermined pauses of time are of increasing durations of from 1 to 2 seconds.

6. A process as set forth in claim 1 which further comprises the step of saturating the prosthesis with an aqueous physiological solution to effect an equalization treatment prior to seeding thereof.

7. A process as set forth in claim 6 wherein the solution is one of a salt solution and a nutrient solution.

8. A process as set forth in claim 1 wherein the deposited cells are epithelial cells.

9. A process as set forth in claim 1 wherein the deposited cells are of different types.

10. A process as set forth in claim 9 wherein the cells of different type form at least two of said layers.

11. A process as set forth in claim 1 wherein the angle of rotation of the prosthesis increased between pauses in multiples of $2\pi$.

* * * * *

UNITED STATES PATENT AND TRADEMARK OFFICE
CERTIFICATE OF CORRECTION

PATENT NO. : 5,037,378
DATED : August 6, 1991
INVENTOR(S) : Werner MULLER, et al.

It is certified that error appears in the above-indentified patent and that said Letters Patent is hereby corrected as shown below:

Col. 1, line 19, change "matrix," to --matrix--.

Col. 1, line 61, change "in prosthesis" to --in at least one uniform layer on the interior surface of the prosthesis--.

Signed and Sealed this

Fourteenth Day of December, 1993

*Attest:*

BRUCE LEHMAN

*Attesting Officer*     Commissioner of Patents and Trademarks